United States Patent

Jobard-Rouppert et al.

Patent Number: 5,322,846
Date of Patent: Jun. 21, 1994

[54] 4-METHYLTHIAZOLE DERIVATIVES, THEIR METHODS OF PREPARATION AND THE PHARMACEUTICAL COMPOSITIONS IN WHICH THEY ARE PRESENT

[75] Inventors: Fabienne Jobard-Rouppert, Vernouillet; Patrick Houziaux, Maule; Jean-Pierre Riffaud, Versailles; Jean-Yves Lacolle, St. Nom la Breteche; Patrick Saur, Chevilly la Rue; Bernard Danree, Poissy, all of France

[73] Assignee: Institut de Recherches Chimiques et Biologiques Appliquees (I.R.C.E.B.A.), Vicq, France

[21] Appl. No.: 916,846

[22] PCT Filed: Feb. 14, 1991

[86] PCT No.: PCT/FR91/00118
§ 371 Date: Oct. 19, 1992
§ 102(e) Date: Oct. 19, 1992

[87] PCT Pub. No.: WO91/12246
PCT Pub. Date: Aug. 22, 1991

[30] Foreign Application Priority Data
Feb. 19, 1990 [FR] France .................. 90 01979

[51] Int. Cl.⁵ .................. A61K 31/495; C07D 417/12
[52] U.S. Cl. .................. 514/252; 544/369; 544/394; 548/186; 548/199; 548/202
[58] Field of Search .................. 544/369; 514/252

[56] References Cited

U.S. PATENT DOCUMENTS

| | | | |
|---|---|---|---|
| 3,787,411 | 1/1974 | Ruschig et al. | 544/284 |
| 3,850,946 | 11/1974 | Edwards | 544/369 |
| 5,120,736 | 6/1992 | Houziaux et al. | 544/369 |

FOREIGN PATENT DOCUMENTS 2209557 7/1974 France .

OTHER PUBLICATIONS

Bogdal et al, *Chemical Abstracts*, vol. 100, No. 156531 (1984).
Toshima et al, *Bull. Chem. Soc. Jpn.* 61, p. 2369 (1988).
Mikkilineni et al, *J. Org. Chem.* 53, p. 6005 (1988).

*Primary Examiner*—Emily Bernhardt
*Attorney, Agent, or Firm*—Dennison, Meserole, Pollack & Scheiner

[57] ABSTRACT

The present invention relates to novel 4-methylthiazole derivatives, to their methods of preparation and to the pharmaceutical compositions in which they are present.

According to the invention, these derivatives have the general formula

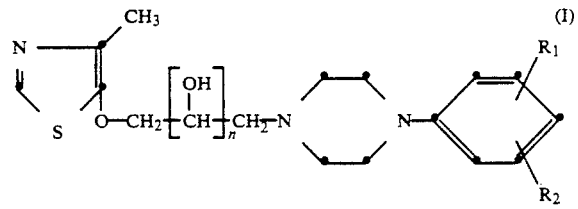

in which n is equal to 0 or 1 and $R_1$ and $R_2$, which are identical or different, are selected from a hydrogen atom, a halogen, a hydroxyl group, a trifluoromethyl group, an alkyl group having from 1 to 4 carbon atoms and an alkoxy group having from 1 to 5 carbon atoms and are useful in the treatment of cardiovascular diseases associated with hyperactivity of the sympathetic nervous system.

3 Claims, No Drawings

4-METHYLTHIAZOLE DERIVATIVES, THEIR METHODS OF PREPARATION AND THE PHARMACEUTICAL COMPOSITIONS IN WHICH THEY ARE PRESENT

The present invention relates to novel 4-methylthiazole derivatives, more precisely amino derivatives of 4-methyl-5-oxythiazole, to their methods of preparation and to pharmaceutical compositions in which they are present.

The compounds according to the invention are 4-methylthiazole derivatives of the general formula

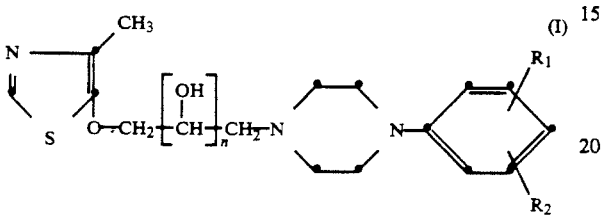

which n is equal to 0 or 1 and $R_1$ and $R_2$, which are identical or different, are selected from a hydrogen atom, a halogen atom, a hydroxyl group, a trifluoromethyl group, an alkyl group having from 1 to 4 carbon atoms and an alkoxy group having from 1 to 5 carbon atoms.

The framework of the invention also includes all the possible optical isomers of the compounds of formula (I) and mixtures thereof.

The framework of the invention also includes the salts of the above-mentioned compounds of formula (I).

In this formula, a halogen atom is preferably a chlorine or fluorine atom.

The alkyl and alkoxy groups can have a linear or branched chain.

An alkyl group having from 1 to 4 carbon atoms is for example a methyl, ethyl, propyl, isopropyl, butyl, isobutyl or tert-butyl group, preferably a methyl or ethyl group.

An alkoxy group having from 1 to 5 carbon atoms is for example a methoxy, ethoxy, propoxy, isopropoxy, butoxy, isobutoxy, tert-butoxy, n-pentoxy, isopentoxy or neopentoxy group, preferably a methoxy, ethoxy, propoxy or isopropoxy group.

The general method of preparing the compounds according to the invention of formula (I), as defined above, in which n is equal to 0 involves a condensation reaction between 5-bromo-4-methylthiazole and the sodium salt of a 2-(4-arylpiperazin-1-yl)ethanol, of the formula

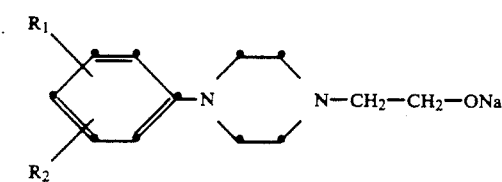

in which $R_1$ and $R_2$ are as defined above.

According to one particular characteristic, the 5-bromo-4-methylthiazole is obtained by brominating 2-amino-4-methylthiazole under conditions which make it possible to obtain 2-amino-5-bromo-4-methylthiazole, and deaminating the resulting 2-amino-5-bromo-4-methylthiazole.

2-Amino-4-methylthiazole is a known product whose method of preparation is described in the literature (Merck Index, 10th edition, no. 454).

The method of preparing the compounds according to the invention of formula (I) in which n is equal to 0 is therefore preferably carried out in three steps in accordance with the reaction scheme described below:

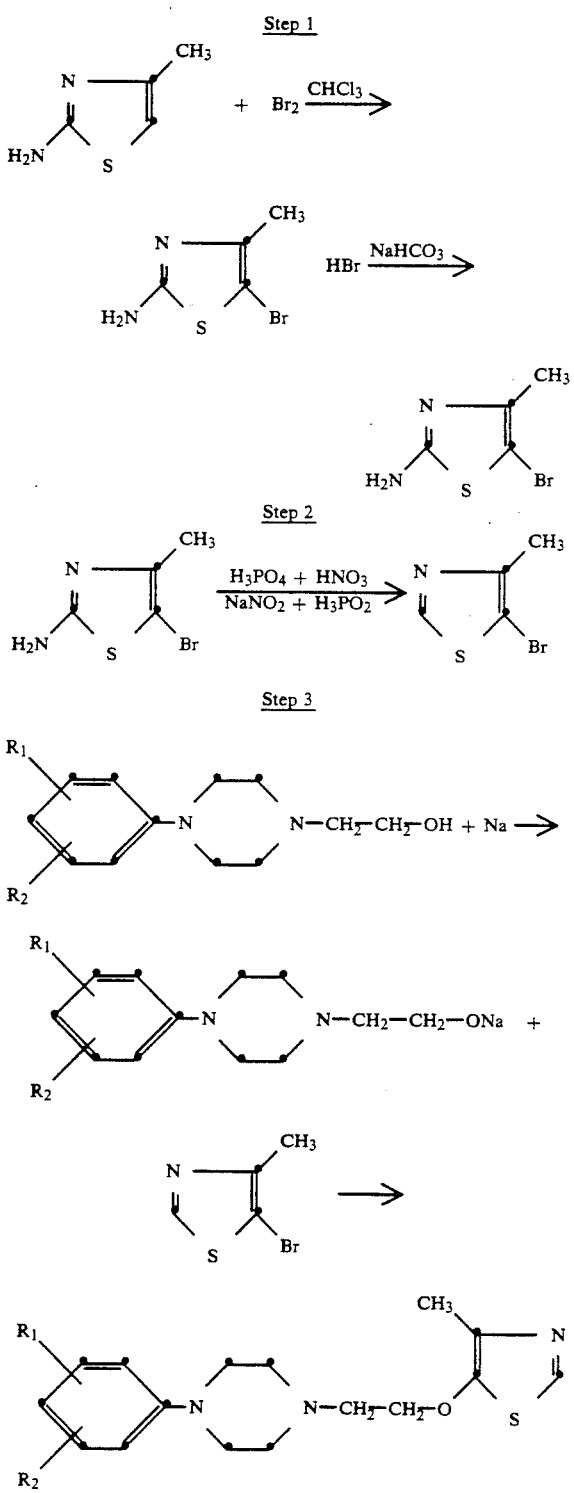

The general method of preparing the compounds according to the invention of formula (I), as defined above, in which n is equal to 1 involves reacting 3-(4-methylthiazolyl-5-oxy)-1,2-epoxypropane with a 4-aryl-piperazine of the formula

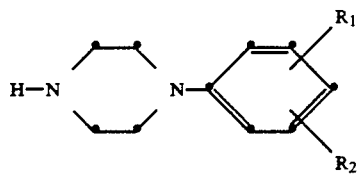

in which $R_1$ and $R_2$ are as defined above.

According to one particular characteristic, the 3-(4-methylthiazolyl-5-oxy)-1,2-epoxypropane is obtained by:

a—reaction of the sodium salt of glycerol acetonide with 5-bromo-4-methylthiazole;

b—acid hydrolysis of the resulting compound under conditions which make it possible to obtain 3-(4-methyl-thiazolyl-5-oxy)propane-1,2-diol; and c—reaction of the compound obtained in step b with ethyl azodicarboxylate and triphenylphosphine.

Glycerol acetonide (or 2,2-dimethyl-1,3-dioxolane-4-methanol), sold by ALDRICH, is a known product whose method of preparation is described for example in Beilstein 19, 65; Merck Index 10, 3236.

Thus the method of preparing the compounds according to the invention of formula (I) in which n is equal to 1 is therefore preferably carried out in four steps in accordance with the reaction scheme described below:

Step 1

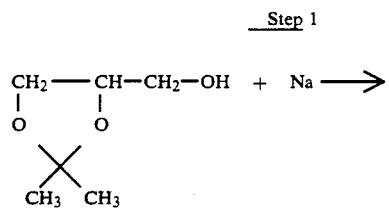

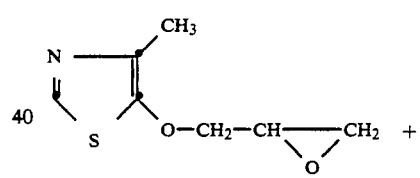

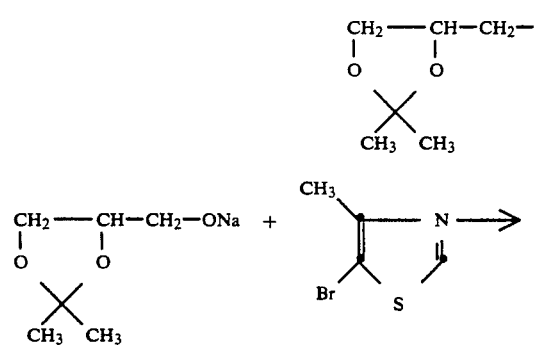

Step 2

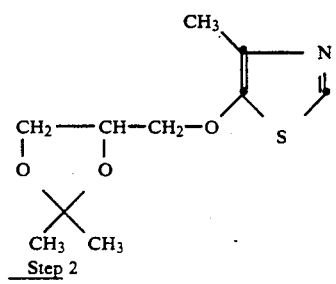

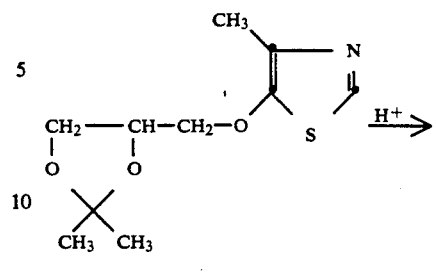

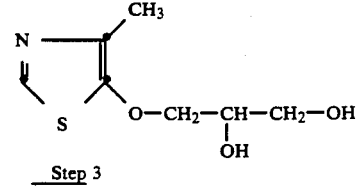

Step 3

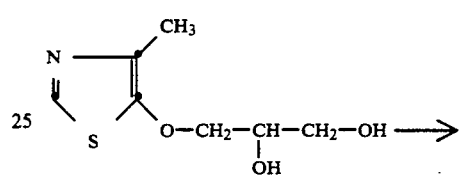

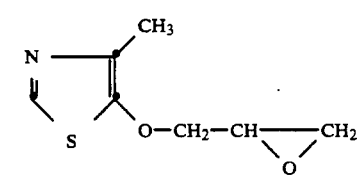

Step 4

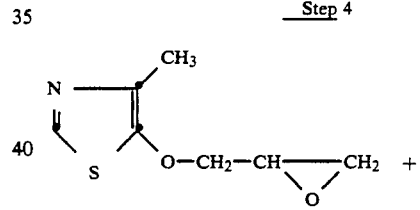

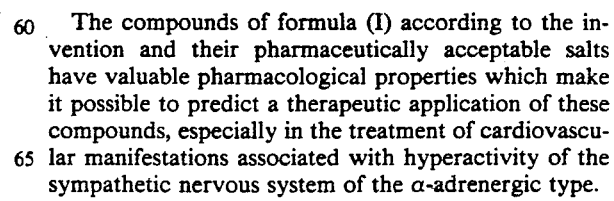

The compounds of formula (I) according to the invention and their pharmaceutically acceptable salts have valuable pharmacological properties which make it possible to predict a therapeutic application of these compounds, especially in the treatment of cardiovascular manifestations associated with hyperactivity of the sympathetic nervous system of the α-adrenergic type.

Thus, according to another feature, the invention also aims to cover novel pharmaceutical compositions which contain at least one compound of formula (I) or a non-toxic addition salt thereof as the active principle, in association with a pharmaceutically acceptable excipient.

The pharmaceutically acceptable salts of the compounds of formula (I) are obtained in a manner known per se by bringing the products of formula (I) into contact with an appropriate amount of a pharmaceutically acceptable acid such as, for example, a mineral acid like hydrochloric acid or sulfuric acid, or an organic acid like citric, tartaric or fumaric acid.

The pharmaceutical compositions according to the invention can generally be prepared by conventional methods and administered in an appropriate pharmaceutical form.

The compounds can be administered orally, for example, in 1 to 3 dosage units per day, at a rate of 2 to 200 mg per dosage unit, depending on the compound, for example in the treatment of cardiovascular manifestations associated with hyperactivity of the sympathetic nervous system of the α-adrenergic type.

According to yet another feature, the invention aims to cover a method of preparing a pharmaceutical composition, which comprises incorporating a pharmaceutically effective amount of at least one compound of formula (I) as defined above, or a non-toxic addition salt of this compound, into a pharmaceutically acceptable excipient.

The invention finally aims to cover a method of treating cardiovascular manifestations associated with hyperactivity of the sympathetic nervous system of the α-adrenergic type, which comprises administering to a mammal, including man and animals, a therapeutically effective amount of at least one compound of formula (I) as defined above, or a pharmaceutically acceptable addition salt of this compound.

The invention will be illustrated with the aid of the following non-limiting Examples:

EXAMPLE 1

Synthesis of 4-methyl-5-[2-(4-o-ethoxyphenylpiperazin-1-yl)ethoxy]thiazole (B 1258)

Step 1: Synthesis of 2-amino-5-bromo-4-methylthiazole

A solution of bromine in chloroform, consisting of 66.7 ml (1.30 mol) of $Br_2$ in 1000 ml of $CHCl_3$, is added dropwise to a solution of 120 g (1.05 mol) of 2-amino-4-methylthiazole in 2300 ml of $CHCl_3$, with stirring.

A precipitate appears during the addition. Stirring is maintained for 48 h.

The reaction medium is then filtered and the hydrobromide is washed with methylene chloride and then with pentane.

The hydrobromide is dissolved in 2000 ml of water and then rendered basic by the addition of 850 ml of a 10% aqueous solution of sodium bicarbonate.

This solution is then extracted with methylene chloride. The organic phase is dried over sodium sulfate. A crystalline residue is obtained after removal of the solvent under vacuum.

Brown crystals: m=155 g (crude yield: 76%)
M.p.$_{KB}$=112°-113° C.
$^1$H NMR (δ ppm, DMSO) 2.05 (s, 3H, $CH_3$); 7.15 (s, 2H, $NH_2$).

Step 2: Synthesis of 4-methyl-5-bromothiazole 70.7 g (0.366 mol) of the 2-amino-5-bromo-4-methylthiazole obtained in step 1 are dissolved in a mixture of nitric acid (65%, 102 ml) and phosphoric acid (85%, 480 ml) and diazotized at between −10° C. and −5° C. with a solution of 39.4 g (0.571 mol) of sodium nitrite in 130 ml of water.

The reaction medium is stirred at this temperature for 30 min. Hypophosphorous acid (50%, 197 ml) is then added slowly to the reaction medium at −10° C. After the addition, the medium is stirred at this temperature for 3 h and the whole is then left overnight at room temperature.

The mixture is neutralized with a 30% aqueous solution of sodium hydroxide (1.670 mol) and then extracted with methylene chloride. The organic phase is dried over sodium sulfate, the solvent is removed by evaporation under vacuum and the oil collected in this way is purified by passing via the hydrochloride and freeing the base again.

Yellow oil: m=31.28 g (yield 48%) $n_D^{27}$: 1.5735

| $C_4H_4BrNS$: | | | | |
|---|---|---|---|---|
| % Calc. | C 26.98 | H 2.26 | Br 44.88 | N 7.87 |
| % Found | C 26.80 | H 2.29 | Br 44.80 | N 7.78 |
| $^1$H NMR (δ ppm, DMSO) | | 2.35(s, 3H, $CH_3$) | | |
| | | 9.05(s, H, Ar). | | |

Step 3

1.4 g (0.061 mol) of sodium are added to 83.5 g (0.33 mol) of 2-(4-o-ethoxyphenylpiperazin-1-yl)ethanol at 40° C. It is necessary to heat at 120° C. for 5 h in order to form the sodium salt.

9.43 g (0.053 mol) of the 4-methyl-5-bromothiazole obtained in step 2 are then introduced into the reaction medium at 60°-65° C., with stirring. This temperature is maintained for 5 h and then raised to 80° C. over 1 h.

The reaction medium, with methylene chloride added, is centrifuged at 3000 rpm for 15 min. After decantation and evaporation of the solvent under vacuum, the 2-(4-o-ethoxyphenylpiperazin-1-yl)ethanol is removed by fractional distillation under reduced pressure. The distillation residue is purified by chromatography on a silica gel column (AcOEt)

The trihydrochloride is prepared in anhydrous ethyl ether by the addition of dry gaseous HCl and then recrystallized from a mixture of isopropanol and pentane.
M.p.$_{KB}$=170° C. (sublimation)
$C_{18}H_{28}Cl_3N_3O_2S$: 456.85

| C.H.N | % Calc. | 47.32 | 6.18 | 9.20 |
|---|---|---|---|---|
| | % Found | 47.34 | 6.23 | 9.05 |

$^1$H NMR (δ ppm, DMSO-$d_6$)

| δ thiazole H | phenyl H | O—$CH_2$ | aliph. $CH_2$ | O—$CH_2$—$CH_2$ |
|---|---|---|---|---|
| 8.85 | 7.00 | 4.60 | 4.05 | 3.10 |
| (s, 1H) | (s, 4H) | (t, 2H) | (q, 2H) | (t, 2H) |
| piperazine $CH_2$ | | thiazole $CH_3$ | | aliph. $CH_3$ |
| 2.80 | | 2.30 | | 1.35 |
| (m, 8H) | | (s, 3H) | | (t, 3H) |

EXAMPLES 2 to 12

The following compounds were prepared using experimental procedures analogous to those described in Example 1, which will be readily apparent to those skilled in the art:

—4-methyl-5-[2-(4-m-trifluoromethylphenylpiperazin-1yl)ethoxy]thiazole (B 1194), —4-methyl-5-[2-(4-phenylpiperazin-1-yl)ethoxy]-thiazole (B 1216),
—4-methyl-5-[2-(4-o-methoxyphenylpiperazin-1-yl)ethoxy]thiazole (B 1223),
—4-methyl-5-[2-(4-p-fluorophenylpiperazin-1-yl)ethoxy]thiazole (B 1227),
—4-methyl-5-[2-[4-(4-chloro-2-methylphenyl)piperazin-1-yl]ethoxy]thiazole (B 1259),
—4-methyl-5-[2-(4-o-fluorophenylpiperazin-1-yl)ethoxy]thiazole (B 1305),
—4-methyl-5-[2-[4-(5-chloro-2-methylphenyl)piperazin-1-yl]ethoxy]thiazole (B 1313),
—4-methyl-5-[2-(4-m-ethoxyphenylpiperazin-1-yl)ethoxy]thiazole (B 1325),
—4-methyl-5-[2-(4-o-propoxyphenylpiperazin-1-yl)ethoxy]thiazole (B 1342),
—4-methyl-5-[2-[4-(6-chloro-2-methylphenyl)piperazin-1-yl]ethoxy]thiazole (B 1366) and
—4-methyl-5-[2-(4-o-hydroxyphenylpiperazin-1-yl)ethoxy]thiazole (B 1430).

The principal data relating to the products synthesized in Examples 1 to 12 have been collated in Table 1.

TABLE No. 1

| Example | B | R'$_2$ (phenyl substitution) | Empirical formula | MW | M.p.$_{KB}$ (°C.) Sublimation | Recrystallization solvent(s) |
|---|---|---|---|---|---|---|
| 2 | 1194 | ** CF$_3$ | C$_{17}$H$_{22}$Cl$_2$F$_3$N$_3$OS | 444.34 | >140 | AcOEt (washing, Δ) |
| 3 | 1216 | *** | C$_{16}$H$_{24}$Cl$_3$N$_3$OS | 412.81 | >110 | IPA/EtOH (1/9) |
| 4 | 1223 | *** CH$_3$—O | C$_{17}$H$_{26}$Cl$_3$N$_3$O$_2$S | 442.82 | 115 | Acetone (washing) |
| 5 | 1227 | *** F | C$_{16}$H$_{23}$Cl$_3$FN$_3$OS | 430.79 | >100 | IPA/AcOEt (85/15) |
| 1 | 1258 | *** C$_2$H$_5$—O | C$_{18}$H$_{28}$Cl$_3$N$_3$O$_2$S | 456.85 | >170 | IPA/pentane |
| 6 | 1259 | ** Cl, CH$_3$ | C$_{17}$H$_{24}$Cl$_3$N$_3$OS | 424.82 | >95 | IPA/pentane |

TABLE No. 1-continued

[Structure: thiazole-CH3/O-CH2-CH2-N(piperazine)N-phenyl(R1,R2).xHCl]

[Structure: phenyl with R1, R'2]

| Example | B | R'2 | Empirical formula | MW | M.p.$_{KB}$ (°C.) Sublimation | Recrystallization solvent(s) |
|---|---|---|---|---|---|---|
| 7 | 1305 | phenyl-F (**) | $C_{16}H_{22}Cl_2FN_3OS$ | 394.34 | >100 | IPA/pentane (95/5) |
| 8 | 1313 | phenyl-Cl,CH3 (**) | $C_{17}H_{24}Cl_3N_3OS$ | 424.82 | >170 | IPA/pentane |
| 9 | 1325 | phenyl-O-C2H5 (**) | $C_{18}H_{27}Cl_2N_3O_2S$ | 420.40 | >120 | EtOH |
| 10 | 1342 | phenyl-O-C3H7 (*) | $C_{19}H_{28}ClN_3O_2S$ | 379.96 | 178 | IPA/hexane (2/1) |
| 11 | 1366 | phenyl-Cl,CH3 (*) | $C_{17}H_{23}Cl_2N_3OS$ | 388.35 | >120 | IPA/hexane Et2O/AcOEt |
| 12 | 1430 | phenyl-OH (none) | $C_{16}H_{22}ClN_3O_2S$ | 355.89 | 180 | IPA/hexane (3/1) |

*Monohydrochloride
**Dihydrochloride
***Trihydrochloride

EXAMPLE 13

Step 1: Synthesis of 3-(4-methylthiazolyl-5-oxy)-propane-1,2-diol acetonide 6.17 g (0.268 mol) of sodium are added to 430 ml of glycerol acetonide. After 3 h 30 min at room temperature and 1 h 30 min at 50° C., 36.8 g (0.207 mol) of 5-bromo-4-methylthiazole are introduced and the reaction medium is heated for 7 h at 110° C.

The 5-bromo-4-methylthiazole can be obtained by following the experimental procedure described in steps 1 and 2 of Example 1.

After filtration of the medium, taking-up with methylene chloride and then concentration under reduced pressure, the compound is purified by fractional distillation under vacuum.

B.p./0.4 mbar=95°-100° C.
$n_D^{27.5}$: 1.5010

$^1$H NMR (δ ppm, CCl$_4$)

| δ thiazole H | 2 CH$_2$—CH | thiazole CH$_3$ | 2 acetonide CH$_3$ |
|---|---|---|---|
| 8.20 | 3.45–4.50 | 2.30 | 1.35 |
| (s, 1H) | (m, 5H) | (s, 3H) | (s, 6H) |

Step 2: Synthesis of 3-(4-methylthiazolyl-5-oxy)-propane-1,2-diol 400 ml of 1N aqueous hydrochloric acid are added to a solution containing 30 g (0.31 mol) of the 3-(4-methylthiazolyl-5-oxy)propane-1,2-diol acetonide obtained in step 1 in 1600 ml of methanol at room temperature.

The reaction medium is stirred for 15 h.

After concentration of the medium to dryness under reduced pressure, the hydrochloride is crystallized from a mixture of isopropanol and ethyl ether. The base is freed by the addition of a 10% solution of sodium bicarbonate and then purified by recrystallization from a mixture of ethyl acetate and pentane (80/20) to give 19.1 g of white crystals.

M.p.$_{KB}$=72°-73° C.

$^1$H NMR (δ ppm, DMSO)

| δ thiazole H | >CH—OH | —CH$_2$—OH | CH$_2$/CH | thiazole CH$_3$ |
|---|---|---|---|---|
| 8.45 | 5 | 4.65 | 3.25–4.20 | 2.25 |
| (s, 1H) | (d, 1H) | (t, 1H) | (m, 5H) | (s, 3H) |

Step 3: Synthesis of 3-(4-methylthiazolyl-5-oxy)-1,2-epoxypropane 12.2 g (0.07 mol) of ethyl azodicarboxylate are added dropwise to a solution containing 10 g (0.053 mol) of the 3-(4-methylthiazolyl-5-oxy)propane-1,2-diol obtained in step 2 and 14 g (0.053 mol) of triphenylphosphine in 200 ml of toluene at room temperature.

The reaction medium is heated for 10 h at 70° C.

After selective crystallization of the dicarbethoxyhydrazine and the triphenylphosphine oxide by the addition of pentane to the reaction medium, the filtrate is concentrated to dryness under reduced pressure and the 3-(4-methylthiazolyl-5-oxy)-1,2-epoxypropane is purified by chromatography on a silica gel column (AcOEt) to give 6.75 g of epoxide in the form of a pale yellow oil.

| IR: | 3080 cm$^{-1}$, | 1560 C=C, C=N | 1260 C—O, | 840 C—O |
|---|---|---|---|---|
| | thiazole | thiazole | thiazole | epoxide |

$^1$H NMR (δ ppm, DMSO)

| δ thiazole H | CH$_2$/CH | thiazole CH$_3$ |
|---|---|---|
| 8.4 | 2.6–4.5 | 2.2 |
| (s, 1H) | (m, 5H) | (s, 3H) |

Step 4: Synthesis of 3-(4-o-propoxyphenylpiperazin-1-yl)-1-(4-methylthiazolyl-5-oxy)propan-2-ol monohydrochloride (B 1395)

2.5 g (0.0113 mol) of o-propoxyphenylpiperazine are added dropwise to a solution containing 1.94 g (0.0113 mol) of the 3-(4-methylthiazolyl-5-oxy)-1,2-epoxypropane obtained in step 3 in 90 ml of ethanol at room temperature.

The reaction medium is heated at 40° C. for 21 h.

The solvent is removed by distillation under reduced pressure to give an oil.

The monohydrochloride is obtained by the addition of a stoichiometric amount of an ethanolic solution of hydrochloric acid, proportioned beforehand, to an ethanolic solution of the base, cooled in an ice bath. After stirring for 1 h and removal of the ethanol by distillation under reduced pressure, the product is crystallized from a mixture of ethyl ether and acetone and then recrystallized from acetone.

White crystals are obtained: 3.21 g.

M.p.$_{KB}$=144°-145° C.

M.p.$_{KB}$ = 144–145° C.
C$_{20}$H$_{30}$ClN$_3$O$_3$S:

| | | | |
|---|---|---|---|
| % Calc. | C 56.13 | H 7.07 | N 9.82 |
| % Found | C 56.50 | H 7.01 | N 9.80 |

$^1$H NMR (δ ppm, DMSO)

| OH | thiazole H | phenyl H | CH$_2$—O |
|---|---|---|---|
| 11.0 | 8.35 | 6.85 | 4.45 |
| (m, 1H) | (s, 1H) | ("s", 4H) | (m, 2H) |
| CH$_2$N piperazine CH$_2$ CH CH$_2$ | thiazole CH$_3$ | propoxy CH$_2$ | propoxy CH$_3$ |
| 3.4 | 2.2 | 1.7 | 1 |
| (m, 13H) | (s, 3H) | (m, 2H) | (t, 3H) |

EXAMPLES 14 to 24

The following compounds were prepared using experimental procedures analogous to those described in Example 13, which will be readily accessible to those skilled in the art:

—3-(4-o-ethoxyphenylpiperazin-1-yl)-1-(4-methylthiazolyl-5-oxy)propan-2-ol (B 1392), —3-(4-o-hydroxyphenylpiperazin-1-yl)-1-(4-methylthiazolyl-5-oxy)propan-2-ol (B 1396), —3-[4-(4-chloro-2-methylphenyl)piperazin-1-yl]-1-(4-methylthiazolyl-5-oxy)propan-2-ol (B 1406), —3-(4-o-isopropoxyphenylpiperazin-1-yl)-1-(4-methylthiazolyl-5-oxy)propan-2-ol (B 1429), —3-(4-o-phenylpiperazin-1-yl)-1-(4-methylthiazolyl-5-oxy)propan-2-ol (B 1431), —3-(4-m-trifluoromethylphenylpiperazin-1-yl)-1-(4-methylthiazolyl-5-oxy)propan-2-ol (B 1489), —3-(4-o-methoxyphenylpiperazin-1-yl)-1-(4-methylthiazolyl-5-oxy)propan-2-ol (B 1510), —3-(4-o-pentoxyphenylpiperazin-1-yl)-1-(4-methylthiazolyl-5-oxy)propan-2-ol (B 1525), —3-(4-m-chlorophenylpiperazin-1-yl)-1-(4-methylthiazolyl-5-oxy)propan-2-ol (B 1548), —3-(4-o-isopentoxyphenylpiperazin-1-yl)-1-(4-methylthiazolyl-5-oxy)propan-2-ol (B 1552) and —3-(4-o-neopentoxyphenylpiperazin-1-yl)-1-(4-methylthiazolyl-5-oxy)propan-2-ol (B 1562).

The formulae and the principal physical properties relating to the products synthesized in Examples 13 to 24 have been collated in Table 2.

TABLE No. 2
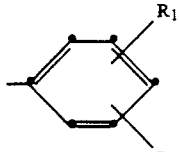
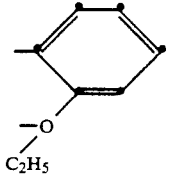
| Example | B | R₂ | Empirical formula | MW | M.p.$_{KB}$ (°C.) Sublimation | Recrystallization solvent(s) |
|---|---|---|---|---|---|---|
| 14 | 1392 | —O—C₂H₅ | $C_{19}H_{28}ClN_3O_3S$ | 413.97 | 149–151 | Acetone |
| 13 | 1395 | —O—C₃H₇ | $C_{20}H_{30}ClN_3O_3S$ | 427.99 | 144–145 | Acetone |
| 15 | 1396 | —OH | $C_{17}H_{24}ClN_3O_3S$ | 385.91 | 110 | EtOH/pentane |
| 16 | 1406 | CH₃ / —Cl | $C_{18}H_{25}Cl_2FN_3O_2S$ | 418.38 | 162–163 | Ethyl acetate |
| 17 | 1429 | (CH₃)₂CH—O— | $C_{20}H_{30}ClN_3O_3S$ | 427.99 | 174–176 | Ethyl acetate/IPA |
| 18 | 1431 | (CH₃)₂CH—CH₂—O— | $C_{21}H_{32}ClN_3O_3S$ | 442.02 | 170–171 | Acetone/IPA |
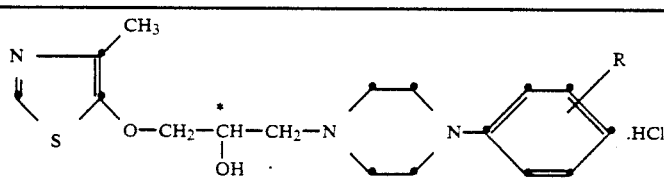

TABLE No. 2-continued

| Example | B | R (substituent) | Empirical formula | MW | M.p.$_{KB}$ (°C.) Sublimation | Recrystallization solvent(s) |
|---------|------|---|-------------------|--------|---------|----------|
| 19 | 1489 | CF$_3$ | C$_{18}$H$_{23}$ClF$_3$N$_3$O$_2$S | 437.91 | 132–134 | AcOEt |
| 20 | 1510 | O—CH$_3$ | C$_{18}$H$_{26}$ClN$_3$O$_3$S | 399.93 | 120–122 | AcOEt/IPA (15/1) |
| 21 | 1525 | O—(CH$_2$)$_4$—CH$_3$ | C$_{22}$H$_{34}$ClN$_3$O$_3$S | 456.04 | 134–136 | AcOEt |
| 22 | 1548 | Cl | C$_{17}$H$_{23}$Cl$_2$N$_3$O$_2$S | 404.35 | 124–126 | AcOEt |
| 23 | 1552 | O—(CH$_2$)$_2$—CH(CH$_3$)$_2$ | C$_{22}$H$_{34}$ClN$_3$O$_3$S | 456.04 | 120–122 | AcOEt |
| 24 | 1562 | O—CH$_2$—C(CH$_3$)$_3$ | C$_{22}$H$_{34}$ClN$_3$O$_3$S | 456.04 | 166–168 | AcOEt |

The toxicity and the pharmacological properties of the products of formula (I) were tested and the results obtained are described below:

I. ACUTE TOXICITY IN MICE

Principle of the Measurement

The products were administered orally in a single dose to male mice with an average weight of 22 g. The mortality was recorded after a 14-day observation period.

The results are expressed in the form of the 50% lethal dose (LD$_{50}$), i.e. the theoretical dose in mg.kg$^{-1}$, administered orally, which causes the death of 50% of the animals.

Results

These are reported in Table 3. The majority of the molecules have an LD$_{50}$ of more than 1 g.kg$^{-1}$. These are therefore products with a low toxicity after a single administration.

II DETERMINATION OF THE ALPHA-BLOCKING ACTIVITY ON ISOLATED RATE VAS DEFERENS

Principle

Stimulation of the postsynaptic alpha-adrenergic receptors by norepinephrine causes contraction of the isolated vas deferens.

The concentration of product in whose presence the norepinephrine concentration must be doubled in order to obtain the same effect as in the absence of said product is determined. The logarithm of this concentration, with the opposite sign, constitutes the pA$_2$ of the products.

Results

The $pA_2$ values reported in Table 4 show that the products behave as competitive norepinephrine antagonists at the alpha-adrenergic receptors.

Their alpha-blocking activity is high since it appears for low concentrations of between $10^{-6}M$ and $10^{-8}M$.

III. DETERMINATION OF THE ADRENOLYTIC ACTIVITY "IN VIVO" IN RATS

Principle of the Measurement

The intravenous injection of norepinephrine (0.4 mg.kg$^{-1}$) into wake male rats causes the death of 100% of the animals. The prior administration of a substance which has an alpha-blocking property makes it possible to reduce this toxicity.

Results

The results are expressed in the form of the 50% effective dose ($ED_{50}$), i.e. the dose in mg.kg$^{-1}$ which protects 50% of the animals (Table 5). The products B 1258, B 1242, B 1392, B 1395, B 1396, B 1429, B 1431, B 1510, B 1525, B 1548 and B 1552 in particular are found to be very active in the whole animals, thereby confirming their action demonstrated in vitro.

IV. DETERMINATION OF THE INHIBITORY ACTIVITY TOWARDS HYPERTENSION IN RABBITS

Principle of the measurement

The blood pressure is measured by catheterization of the left carotid artery of anesthetized male rabbits. An increase in blood pressure is induced by an intravenous injection of norepinephrine. This hypertension can be inhibited by the prior administration of molecules with an alpha-blocking potential.

Only the compounds B 1216, B 1258, B 1305, B 1342, B 1392, B 1395 and B 1431 were tested on this model.

Results

These are presented in Table 6 in the form of the 50% inhibitory dose ($ID_{50}$), which is defined as the dose of product which, when administered intravenously, causes a 50% inhibition of the hypertension induced by norepinephrine. The compound B 1395 is particularly effective with an active dose of less than 1 mg.kg$^{-1}$.

V. DETERMINATION OF THE CARDIOVASCULAR ACTIVITY

Principle of the Measurement

The cardiovascular effects of three products were studied in rats anesthetized with pentobarbital and placed under artificial respiration. The femoral blood pressure and the heart rate are recorded by means of a GOULD-BRUSH apparatus.

The products are administered intravenously in increasing doses. Three animals are tested per product. The dose which causes a 25% drop in average blood pressure ($ED_{25}$) was evaluated for each product and compared with nicardipine 1 to 5 min after administration.

Results

The products have dose-dependent hypotensive effects but have little or no effect on the heart rate (Table 7). The most hypotensive in terms of the effective dose is B 1395 ($ED_{25}$ of 0.004 mg.kg$^{-1}$). The $ED_{25}$ values determined 5 min after injection make it possible to place the hypotensive potential of the products B 1395, B 1396, B 1431, B 1552 on a level with that of nicardipine.

TABLE No. 7

| Product | Blood pressure: Hypotension | | Heart rate |
|---|---|---|---|
| | $ED_{25}$ at 1 minute (mg.kg$^{-1}$ I. V.) | $ED_{25}$ at 5 minutes (mg.kg$^{-1}$ I. V.) | Maximum effect in % |
| B 1258 | 0.8 | 1 | −5.6 |
| B 1392 | 0.024 | 0.048 | −11.2 |
| B 1395 | 0.004 | 0.1 | −4 |
| B 1396 | 0.008 | 0.06 | 0 |
| B 1429 | 0.016 | 0.03 | −5.1 |
| B 1431 | 0.1 | 0.24 | −12 |
| B 1510 | 0.01 | 0.01 | −6 |
| B 1525 | 0.04 | 0.04 | −8 |
| B 1552 | 0.12 | 0.25 | −7.9 |
| NICARDIPINE | 0.0015 | 0.2 | 0 |

These data make it possible to predict a good therapeutic activity of the compounds of formula (I) in cardiovascular manifestations associated with hyperactivity of the sympathetic nervous system of the alpha-adrenergic type.

TABLE 3

| Acute toxicity of the various compounds in mice by oral administration | | | | | | | | | | | | |
|---|---|---|---|---|---|---|---|---|---|---|---|---|
| B CODE | B 1194 | B 1216 | B 1223 | B 1227 | B 1258 | B 1259 | B 1305 | B 1313 | B 1325 | B 1342 | B 1366 | B 1392 |
| $LD_{50}$ mg.kg$^{-1}$ | >1000 | >1000 | >1000 | 1000 | >1000 | 630 | >1000 | 770 | >1000 | >1000 | 740 | 260 |
| B CODE | B 1395 | B 1396 | B 1406 | B 1429 | B 1430 | B 1431 | B 1489 | B 1510 | B 1525 | B 1548 | B 1552 | B 1562 |
| $LD_{50}$ mg.kg$^{-1}$ | 515 | 315 | 515 | 428 | 305 | 1000 | >1000 | 235 | >1000 | >500 | >1000 | >1000 |

TABLE 4

| Alpha-blocking activity of the products towards norepinephrine on isolated rat vas deferens | | | | | | | | | | | | |
|---|---|---|---|---|---|---|---|---|---|---|---|---|
| B CODE | B 1194 | B 1216 | B 1223 | B 1227 | B 1258 | B 1259 | B 1305 | B 1313 | B 1325 | B 1342 | B 1366 | B 1392 |
| $pA_2$ | 5.59 | 7.05 | 6.57 | <6 | 7.80 | 5.87 | 7.09 | 7.09 | 6.09 | 7.79 | <6 | 7.88 |
| B CODE | B 1395 | B 1396 | B 1406 | B 1429 | B 1430 | B 1431 | B 1489 | B 1510 | B 1525 | B 1548 | B 1552 | B 1562 |
| $pA_2$ | 7.70 | 6.50 | 6.40 | 8.34 | 6.64 | 8.13 | — | 7.67 | 8.10 | — | 7.64 | — |

TABLE 5

Adrenolytic activity of the products on the lethal effect of norepinephrine in rats
($ED_{50}$ = 50% effective dose)

| B CODE | B 1194 | B 1216 | B 1223 | B 1227 | B 1258 | B 1259 | B 1305 | B 1313 | B 1325 | B 1342 | B 1366 | B 1392 |
|---|---|---|---|---|---|---|---|---|---|---|---|---|
| $ED_{50}$ mg.kg$^{-1}$ | 200 | 33 | 13 | 30 | 6.5 | 45 | 35 | 109 | 49 | 4.0 | 100 | 0.3 |

| B CODE | B 1395 | B 1396 | B 1406 | B 1429 | B 1430 | B 1431 | B 1489 | B 1510 | B 1525 | B 1548 | B 1552 | B 1562 |
|---|---|---|---|---|---|---|---|---|---|---|---|---|
| $ED_{50}$ mg.kg$^{-1}$ | 0.2 | 0.6 | 8.1 | 0.5 | 8.3 | 0.4 | 59.7 | 0.52 | 1.27 | 15.8 | 1.55 | — |

TABLE 6

Inhibitory action of the compounds on the hypertension induced by norepinephrine in anesthetized rabbits
($ID_{50}$ = 50% inhibitory dose)

| B CODE | B 1194 | B 1216 | B 1223 | B 1227 | B 1258 | B 1259 | B 1305 | B 1313 | B 1325 | B 1342 | B 1366 | B 1392 |
|---|---|---|---|---|---|---|---|---|---|---|---|---|
| $ID_{50}$ mg.kg$^{-1}$ | — | >3 | — | — | 5.6 | — | 3.0 | — | — | 7.3 | — | 2.6 |

| B CODE | B 1395 | B 1396 | B 1406 | B 1429 | B 1430 | B 1431 |
|---|---|---|---|---|---|---|
| $ID_{50}$ mg.kg$^{-1}$ | 0.2 | — | — | — | — | — |

What is claimed is:

1. 4-methylthiazole compounds of the formula

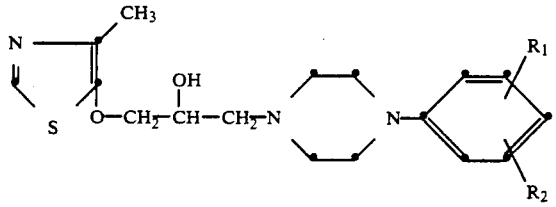

in which $R_1$ and $R_2$, which are identical or different, are selected from the group consisting of a hydrogen atom, a halogen, a hydroxyl group, a trifluoromethyl group, an alkyl group having from 1 to 4 carbon atoms and an alkoxy group having from 1 to 5 carbon atoms, or pharmaceutically acceptable salts thereof.

2. A compound of formula (I) according to claim 1, selected from the group consisting of:
—3-(4-o-ethoxyphenylpiperazin-1-yl)-1-(4-methylthiazolyl-5-oxy)propan-2-ol,
—3-(4-o-hydroxyphenylpiperazin-1-yl)-1-(4-methylthiazolyl-5-oxy)propan-2-ol,
—3-[4-(4-chloro-2-methylphenyl)piperazin-1-yl]-1-(4-methylthiazolyl-5-oxy)propan-2-ol,
—3-(4-o-isopropoxyphenylpiperazin-1-yl)-1-(4-methylthiazolyl-5-oxy)propan-2-ol,
—3-(4-o-isobutoxyphenylpiperazin-1-yl)-1-(4-methylthiazolyl-5-oxy)propan-2-ol,
—3-(4-m-trifluoromethylphenylpiperazin-1-yl)-1-(4-methylthiazolyl-5-oxy)propan-2-ol,
—3-(4-o-methoxyphenylpiperazin-1-yl)-1-(4-methylthiazolyl-5-oxy)propan-2-ol,
—3-(4-o-pentoxyphenylpiperazin-1-yl)-1-(4-methylthiazolyl-5-oxy)propan-2-ol,
—3-(4-m-chlorophenylpiperazin-1yl)-1-(4-methylthiazolyl-5-oxy)propan-2-ol,
—3-(4-o-isopentoxyphenylpiperazin-1-yl)-1-(4-methylthiazolyl-5-oxy)propan-2-ol and
—3-(4-o-neopentoxyphenylpiperazin-1-yl)-1-(4-methylthiazolyl-5-oxy)propan-2-ol.

3. A pharmaceutical composition which contains at least one compound according to claim 1 or 2 as the active ingredient, in association with a pharmaceutically acceptable, non-toxic vehicle or carrier.

* * * * *